United States Patent [19]

Osswald

[11] Patent Number: 5,034,382

[45] Date of Patent: Jul. 23, 1991

[54] TOPICAL COMPOSITION FOR TREATING HERPES WITH ADENOSINE

[75] Inventor: Hartmut Osswald, Waldkirch, Fed. Rep. of Germany

[73] Assignee: Goedecke A.G., Berlin, Fed. Rep. of Germany

[21] Appl. No.: 357,691

[22] Filed: May 25, 1989

Related U.S. Application Data

[63] Continuation of Ser. No. 193,172, May 9, 1988, abandoned, which is a continuation of Ser. No. 780,364, Sep. 26, 1985, abandoned, which is a continuation-in-part of Ser. No. 610,209, May 14, 1984, abandoned.

[30] Foreign Application Priority Data

May 27, 1983 [DE] Fed. Rep. of Germany ....... 3319282

[51] Int. Cl.$^5$ .............................................. A61K 31/70
[52] U.S. Cl. ..................................................... 514/46
[58] Field of Search .......................................... 514/46

[56] References Cited

U.S. PATENT DOCUMENTS 3,666,856  5/1972  Elion et al. ........................... 536/26
3,948,883  4/1976  Ranganathan ....................... 536/26
4,044,122  8/1977  Sklar ..................................... 514/47

FOREIGN PATENT DOCUMENTS 3319282A  11/1984  Fed. Rep. of Germany ........ 514/46
2080682   2/1982  United Kingdom ................ 424/145

OTHER PUBLICATIONS

Bauer, Chemotherapy of Virus Diseases, vol. 1, 1972, p. 259.

*Primary Examiner*—Jerome D. Goldberg
*Attorney, Agent, or Firm*—Elizabeth M. Anderson

[57] ABSTRACT

The invention is concerned with the application of adenosine in the form of topically applicable pharmaceutical preparations for controlling herpes, in particular herpes labialis, herpes zoster, and herpes genitalis. The preparations are applied thinly several times daily to the affected skin or mucous areas. The active substance concentration should be in the region of 5-30%. Anhydrous preparations such as powder or anhydrous ointments have proven to be particularly effective and are surprisingly rapid in promoting healing.

1 Claim, No Drawings

TOPICAL COMPOSITION FOR TREATING HERPES WITH ADENOSINE

CROSS-REFERENCE TO RELATED APPLICATION

This is a continuation of U.S. Ser. No. 07/193,172 filed May 9, 1988, abandoned, which is a continuation of U.S. Ser. No. 06/780,364 filed Sept. 26, 1985, abandoned, which is a continuation of U.S. Ser. No. 06/780,364 now abandoned which is a continuation-in-part application of U.S. Ser. No. 610,209 filed May 14, 1984 abandoned.

BACKGROUND OF THE INVENTION

Adenosine is a well-known nucleoside which plays a significant role in the metabolism in the form of its phosphates.

However, adenosine has not been significant in the past as a pharmaceutical because, inter alia, it is metabolized extremely quickly upon enteral and parenteral administration. Topical application of adenosine has been totally unknown up to present.

It has not been found that adenosine, when applied topically, surprisingly demonstrates an excellent effect on controlling various types of herpes, in particular herpes labialis, herpes zoster, and herpes genitalis.

SUMMARY OF THE INVENTION

Accordingly the present invention relates to a topical pharmaceutical composition for controlling herpes infections comprising an effective amount of adenosine and a pharmaceutically acceptable neutral carrier.

The present invention also relates to a method for controlling herpes infections which comprises administering to the skin of a subject suffering therefrom an effective amount of a topical composition containing adenosine and a pharmaceutically acceptable neutral carrier.

DETAILED DESCRIPTION OF PREFERRED EMBODIMENTS

According to the invention adenosine is mixed in a concentration of approximately 5–30%, preferably 10–20, with a pharmaceutically acceptable neutral carrier and applied thinly 3–10 times daily to affected skin areas. Characteristically it is possible to determine successful treatment as early as 12 hours after commencement of treatment by a reduction in pain and sensitivity upon touching the diseased areas. In many cases pain is completely eliminated already during the first day of treatment. As neutral carriers, there enter into consideration any basic materials usually employed in ointments, creams, lotions, sprays, powders, or similar preparations. Examples of these are: alcohol, propylene glycol, glycerol, cetostearyl alcohol, vaseline, wool alcohols, wool fat, hard fats, talcum, and optionally preservatives such as PHB ester or sorbic acid.

However, such preparations are preferably used which ensure that the treated skin areas remain as long as possible in contact with the active substance and which are strongly adhesive to the skin surface.

Moreover, it is favorable for the treatment if the skin areas are maintained as dry as possible, with the result that from this aspect powder, anhydrous ointments or lipsticks, and other anhydrous preparations are particularly recommended. The mode of action of the preparations of the invention has not yet been clarified. However, it has been presumed that adenosine inhibits the multiplication of herpes viruses in the host cells.

The particular advantage of topically applicable pharmaceutical preparations is that they allow very high active substance concentrations to be administered exclusively to the diseased skin area. According to the invention no systemic effects of the active substance are to be anticipated due to the quick metabolism of adenosine. The application according to the invention differs in this from that of well-known virustatic agents which partially exhibit considerable systemically-conditioned side-effects.

The subject of the invention is correspondingly a preparation to be applied externally, wherein adenosine is contained as active substance.

A further subject of the invention is the application of adenosine for controlling herpes.

The following examples are given for the purpose of illustrating the invention:

EXAMPLE 1

Twenty g adenosine are mixed with 80 g wool alcohol ointment. The ointment obtained may be applied thinly several times daily to the skin or mucous areas affected by herpes.

EXAMPLE 2

Ten g adenosine are dissolved in a mixture of 17.5% ethanol and 62.5 g purified water under mild heat. Ten g glycerol are added to this solution and the solution obtained is filtered through a membrane filter with a pore diameter of 20 μm.

There is obtained a clear solution which remains sterile due to the alcohol content. The affected skin area is treated by brushing with the solution several times daily.

EXAMPLE 3

Ten g adenosine are dissolved in 70 g warm water to which a preservative has optionally been added, and processed to a lotion with 5 g zinc oxide, 5 g talcum, and 20 g glycerol. Zinc oxide and talcum are mixed and sieved well prior to application and subsequently heated for one hour to 180° C. in a thin layer in a drying cabinet.

The obtained lotion is applied thinly to affected skin areas several times daily after dislodging.

EXAMPLE 4

Twenty g adenosine are worked into 80 g of an anhydrous ointment base. The ointment base is prepared as follows:

Components

Aerosil ® 8.0 g
isopropylmyristate
isopropylpalmitate
paraffin (viscous)
up to 100.0 g.

The liquid components are mixed. In part of this Aerosil ® is triturated to a smooth gel; the remaining solution is gradually added to this gel while stirring.

Following homogenization the anhydrous ointment obtained is filled into bottles under sterile conditions. It is applied thinly several times daily to affected skin areas.

EXAMPLE 5

Fifteen g finely ground adenosine are intensively mixed with 85 g of a powder base consisting of 48% talcum, 50% starch (nonswelling), and 2.0% Aerosil ® in a dry state and passed through a fine sieve (ISO No. 1000). A powder with a grain size of 50μ is obtained, which is applied thinly several times daily to affected skin areas.

EXAMPLE 6

Eighty g hard fat are melted at 40° C. Ten g isopropylmyristate together with 10 g adenosine are stirred into the molten mass. The whole mass is subsequently very finely ground in a colloid mill and poured into cylindrical forms at a temperature of 33°–35° C. as a creamy molten mass.

The sticks obtained are placed in an applicator for ease of handling. The medical lipstick obtained may be used several times daily for treating affected skin areas.

THERAPY REPORT

In order to demonstrate the unexpected anti-herpes activity of Adenosine, the following cases have been treated with topical compositions of Adenosine:

1. Treatment of Herpes Labialis

Eight patients were treated with composition prepared according to Example 1 with 20 g of adenosine mixed with 100 g wool alcohol ointment and applying it thinly to the affected areas 8–10 times daily.

All patients were suffering from clearly recognized herpes labialis.

In 6 patients the vesicles were still tense and in 2 patients the vesicles were oozing.

Herpes labialis normally persists for more than 6 days after appearance of tense vesicles.

Table I shows the therapy success.

TABLE I

Complete healing of vesicles occurs within Z days (day 1 denotes day after beginning of treatment and after onset of the lesions).

| Patient | Day (Z) | | | | | | | |
|---|---|---|---|---|---|---|---|---|
| | 1 | 2 | 3 | 4 | 5 | 6 | 7 | 8 |
| 1 | | | | G | | | | |
| 2 | | | | G | | | | |
| 3 | | | | G | | | | |
| 4 | | | | G | | | | |
| 5 | | | | G | | | | |
| 6 | | | | G | | | | |
| 7 | | | | | O | | | |
| 8 | | | | | O | | | |

G = patients showing tense vesicles on the lips
O = patients showing oozing vesicles on the lips
= average persistence of untreated herpes labialis according to Dermatologie and Venerologie by E. KEINING + O. BRAUN-FALCO; Lehmanns Verlag Munich 1969 page 35.

2. Treatment of Herpes Labialis

Five patients were treated with composition prepared according to Example 1 containing 10 g of adenosine mixed with 100 g wool alcohol ointment and applying it thinly to the affected areas 3 times daily after each meal.

Acute herpes labialis had been diagnosed in all patients.

In one patient herpes lesions occurred between the fingers of the right hand, on the thigh and on the knee area. The patient had been previously treated with Virunguent ®, therefore this case will not be included in Table II.

Table II shows the therapy success.

TABLE II

| Patient | Day (Z) | | | | | | | |
|---|---|---|---|---|---|---|---|---|
| | 1 | 2 | 3 | 4 | 5 | 6 | 7 | 8 |
| 1 | | | | O | | | | |
| 2 | | | G | | | | | |
| 3 | | | | | O | | | |
| 4 | | | | | O | | | |

G = patients showing tense vesicles on the lips
O = patients showing oozing vesicles on the lips
= average persistence of untreated herpes labialis

3. Treatment of Herpes Zoster in 4 Patients Applying 20% Adenosine Ointment as Prepared According to Example 1 a) Case 1: K. C., born in 1924, female
Diagnosis: Necrotizing, exulcerating herpes zoster thoracalis
Duration of treatment: 15 days
Result: Good therapeutic response, almost no scarring. Mild, recurrent lesions 6 months after treatment.

b) Case 2: M. E., born in 1930, female
Diagnosis: Herpes zoster thoracalis
Duration of treatment: 15 days
Result: Complete healing, no scarring.

c) Case 3: D. M., born in 1932, male
Diagnosis: Herpes thoracalis
Duration of treatment: 14 days
Result: Initially distinct increase of herpes lesions and exacerbation followed by healing without scarring or pain.

d) Case 4: R. E., born in 1935, female
Diagnosis: Herpes zoster inguinalis
Duration of treatment: 8 days
Result: Healing, no scarring or complaints.

These 4 cases clearly demonstrate that healing of herpes zoster occurs within 15 days at the latest after treatment with adenosine ointment (20%). According to E. KEINING and O. BRAUN-FALCO, loc. cit. page 41, up to now healing cannot be expected before 3 to 5 weeks.

The reports mentioned under 1–3 substantiate that duration of herpes infections is drastically reduced after treatment with adenosine (10–20%).

I claim:

1. A method for controlling herpes labialis or herpes zoster infections which comprises administering to the skin of a patient suffering therefrom an antivirally effective amount of a topical composition containing 5–30% of adenosine and a pharmaceutically acceptable neutral carrier in the form of an anhydrous ointment or an hydrous lipstick.

* * * * *